(12) United States Patent
Tabada et al.

(10) Patent No.: US 8,183,111 B1
(45) Date of Patent: May 22, 2012

(54) METHOD OF FABRICATING CONDUCTIVE ELECTRODES ON THE FRONT AND BACKSIDE OF A THIN FILM STRUCTURE

(75) Inventors: Phillipe J. Tabada, Roseville, CA (US); Melody Tabada, legal representative, Roseville, CA (US); Satinderpall S. Pannu, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 12/959,232

(22) Filed: Dec. 2, 2010

Related U.S. Application Data

(60) Provisional application No. 61/266,003, filed on Dec. 2, 2009, provisional application No. 61/285,874, filed on Dec. 11, 2009.

(51) Int. Cl.
*H01L 21/336* (2006.01)
(52) U.S. Cl. ........ 438/261; 438/259; 438/260; 438/618; 438/672
(58) Field of Classification Search .......... 438/618–624, 438/259–261, 270–271, 637–638, 672–673
See application file for complete search history.

(56) References Cited

U.S. PATENT DOCUMENTS

| | | | |
|---|---|---|---|
| 2007/0052086 A1* | 3/2007 | Oi et al. | 257/698 |
| 2009/0305502 A1* | 12/2009 | Lee et al. | 438/667 |
| 2011/0241205 A1* | 10/2011 | Kirby et al. | 257/738 |

* cited by examiner

*Primary Examiner* — Dung A. Le
(74) *Attorney, Agent, or Firm* — James S. Tak

(57) ABSTRACT

A method of fabricating a thin film device having conductive front and backside electrodes or contacts. Top-side cavities are first formed on a first dielectric layer, followed by the deposition of a metal layer on the first dielectric layer to fill the cavities. Defined metal structures are etched from the metal layer to include the cavity-filled metal, followed by depositing a second dielectric layer over the metal structures. Additional levels of defined metal structures may be formed in a similar manner with vias connecting metal structures between levels. After a final dielectric layer is deposited, a top surface of a metal structure of an uppermost metal layer is exposed through the final dielectric layer to form a front-side electrode, and a bottom surface of a cavity-filled portion of a metal structure of a lowermost metal layer is also exposed through the first dielectric layer to form a back-side electrode.

13 Claims, 5 Drawing Sheets

METHOD OF FABRICATING CONDUCTIVE ELECTRODES ON THE FRONT AND BACKSIDE OF A THIN FILM STRUCTURE

I. CLAIM OF PRIORITY IN PROVISIONAL APPLICATION

This application claims priority in provisional application filed on Dec. 2, 2009, entitled "Different Methods of Fabricating Conductive Electrodes on the Front and Backside of Polymer, Semiconductor, Metal and Dielectric Based Devices" Ser. No. 61/266,003, by Phillipe J. Tabada et al, and in provisional application filed on Dec. 11, 2009, entitled "Fabrication of a Hybrid Silicone-Parylene Neural Prosthetic Device" Ser. No. 61/285,874, by Phillipe J. Tabada et al, both of which are incorporated by reference herein.

II. FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

III. FIELD OF THE INVENTION

The present invention relates to thin film structures and fabrication methods, and more particularly to ion mill-etched metal-on-polymer thin film devices having both front and backside electrodes and methods of fabricating such structures.

IV. BACKGROUND OF THE INVENTION

Thin film devices are often required to electrically connect directly to different components located on opposite sides (i.e. front and back) of the device, or otherwise have electrodes or electrical contacts available on opposite sides of the device. However, conventional MEMS techniques used to fabricate the polymer, semiconductor, metal and/or dielectric material-based thin film structures of such devices typically produce electrical connections/electrodes only on a top surface (i.e. a front side/face) of the device. Consequently, in order to electrically connect such devices to components located on opposite sides of the device, previous solutions required producing two top-side electrodes on opposite ends of the device and manually bending or folding the device to face the two electrodes in opposite directions. However, this method has been known to lead to failure in the metalized structures to produce an open circuited device. The physical stress involved in folding the substrate of the device can cause the metalized structures to crack and fail.

As such, there is a need for a thin film device having front and backside electrodes/contacts integrally formed without bending or otherwise deforming the device, and a method of fabricating such devices.

V. SUMMARY OF THE INVENTION

One aspect of the present invention includes a method of fabricating a thin film structure having conductive electrodes on both front and back sides thereof, comprising: forming a top-side cavity on a first dielectric layer; depositing a metal layer on the first dielectric layer so that a portion of the metal layer fills the cavity; etching portions of the metal layer down to the first dielectric layer to form a defined metal structure which includes the cavity-filled portion of the metal layer; depositing a second dielectric layer on the defined metal structure and exposed portions of the first dielectric layer; exposing a top surface of a defined metal structure of an uppermost metal layer to form a front-side electrode; and exposing a bottom surface of a cavity-filled portion of a defined metal structure of a lowermost metal layer to form a back-side electrode.

Another aspect of the present invention includes a method of fabricating a thin film structure having conductive electrodes on both front and back sides thereof, comprising: depositing a release layer on a substrate; depositing a first dielectric layer on the release layer; forming a top-side cavity on the first dielectric layer so as to extend completely through the first dielectric layer down to the release layer; depositing a metal layer on the first dielectric layer so that a portion of the metal layer fills the cavity; etching portions of the metal layer down to the first dielectric layer to form a defined metal structure which includes the cavity-filled portion of the metal layer; depositing a second dielectric layer on the defined metal structure and exposed portions of the first dielectric layer; forming at least one additional level of metal and dielectric layers on the second dielectric layer by, for each additional level: forming a via cavity extending completely through the dielectric layer down to the defined metal structure, so that a via is formed when the another metal layer is deposited on the previous dielectric layer with a portion of the another metal layer filling the via cavity; depositing another metal layer on a previous dielectric layer; etching portions of the another metal layer down to the previous dielectric layer to form another defined metal structure; depositing another dielectric layer on the another defined metal structure and exposed portions of the previous dielectric layer, whereby the uppermost metal layer is different from the lowermost metal layer; exposing a top surface of a defined metal structure of an uppermost metal layer to form a front-side electrode; and removing the release layer to release the substrate and expose the bottom surface of the cavity-filled portion of the defined metal structure of the lowermost metal layer as a back-side electrode.

Generally, the present invention is directed to methods of fabricating a device having a thin film structure and integrally formed conductive front and backside conductive electrodes or electrical pads. Integrally forming the front and backside electrodes to face in opposite directions avoids the need to bend or fold the device which can lead to failure. Single or multi-level metal-on-dielectric thin film devices may be fabricated according the present invention, described generally as follows. Top-side cavities are first formed on a first dielectric layer, followed by the deposition of a metal layer on the first dielectric layer to fill the cavities. Defined metal structures are etched from the metal to layer to include the cavity-filled metal, followed by depositing a second dielectric layer over the metal structures. Additional levels of defined metal structures may be formed in a similar manner with vias connecting metal structures between levels. After a final dielectric layer is deposited, a top surface of a metal structure of an uppermost metal layer is exposed through the final dielectric layer to form a front-side electrode, and a. bottom surface of a cavity-filled portion of a metal structure of a lowermost metal layer is also exposed through the first dielectric layer to form a back-side electrode.

One example method of the present invention uses various back etch techniques that exposes the bottom surface of the cavity-filled portion of the lowermost metal layer/level (i.e. the conductive electrical pads) after the device has been released from the substrate material. And in another method of the present invention metal, water soluble and/or solvent soluble release layer is used to separate the substrate from the device which exposes the bottom surface of the cavity-filled portion of the lowermost metal layer/level.

The method of the present invention invention can be used to fabricate such thin film structures as high density, flexible and durable electrode arrays for use in applications such as for example high density neural stimulation and sensing using microelectrode neural probes to provide a direct electrical interface with the neurons of a biological entity's nervous system. In particular, whereas current neural electrode arrays produced using conventional MEMS techniques have exposed metal pads (e.g. signal recording or stimulation sites) located on a top side of rigid silicon shanks, neural electrode arrays fabricated according to the present invention have electrodes on both front and back surfaces, which can stimulate or record a larger population of neurons. Furthermore, a wide variety of sensors and electronics similar to but not limited to chemical or biological sensors can also be fabricated using a similar arrangement of front and back side sensing elements.

VI. BRIEF DESCRIPTION OF THE DRAWINGS

The accompanying drawings, which are incorporated into and form a part of the disclosure, are as follows.

VII. DETAILED DESCRIPTION

Turning now to the drawings, FIGS. 1-6 together show a first example embodiment of a method of fabricating a thin film structure having conductive electrodes on the front and backsides. In particular, six progressive stages are shown for producing an example single-level thin film structure, i.e. a thin film structure having a single layer of defined metal structures embedded between dielectric layers. It is appreciated however that additional layers of defined metal structures may be formed to produce a multi-level thin film structure and device, described in detail below.

Figure 1:
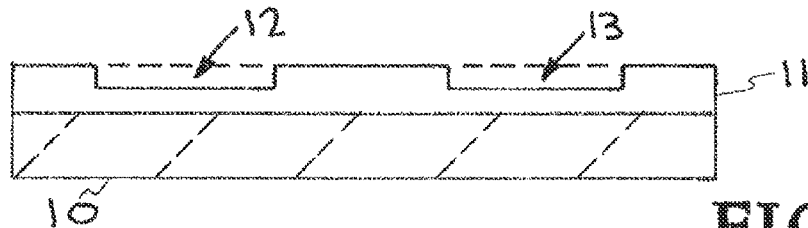
FIGS. 1-6 show six progressive stages of an example embodiment of a method of fabricating an example single-level thin film structure having conductive electrodes on the front and backsides.

FIG. 1 shows a first thin-film dielectric layer 11 deposited on a substrate 10 which may be a silicon, metal, glass or ceramic substrate. For this and subsequent dielectric layers, it is appreciated that any desired dielectric layer material may be used, such as but not limited to parylene, polyimide, polyethylene, polyurethane, silicon, silicon dioxide, silicon nitride, silicon carbide, quartz, boro-silicate glass, soda lime, etc. And deposition of the dielectric layer 11 (and other subsequent dielectric layers) may be performed using conventional thin film deposition techniques, such as but not limited to spin, spray, sputtering, electroplating and/or evaporation techniques. The thickness of the thin film dielectric layer can range, for example, from 1 nm to 10 mm. The dielectric layer may then be placed under a temperature curing cycle if necessary.

FIG. 1 also shows the formation of two top-side cavities 12 and 13 formed on a top side surface of the first dielectric layer 11, such as by using conventional photolithographic techniques to define a photoresist etch mask (not shown), followed by wet and/or dry etch techniques like but not limited to an $O_2$ plasma etch (not shown). It is appreciated that other subsequent dielectric layers may also be etched using the same or similar technique. It is also appreciated that while the "top-side" descriptor for the cavities 12 and 13 is an arbitrary designation of the structure's orientation, it is particularly used herein and in the Claims to indicate the side where (and the direction from which) deposition is performed. In any case, FIG. 1 particularly shows that the top-side cavities 12 and 13 are etched so that they extend only partially through the first dielectric layer 11, and not completely through it. For example only 10% to 90% of the first dielectric may be removed so that the depth of the cavity is less than the thickness of the first dielectric layer. This will allow the exposure of the subsequently formed electrodes while keeping the metal interconnects passivated with the first dielectric layer when the final backside etch occurs at a final stage.

Figure 23:
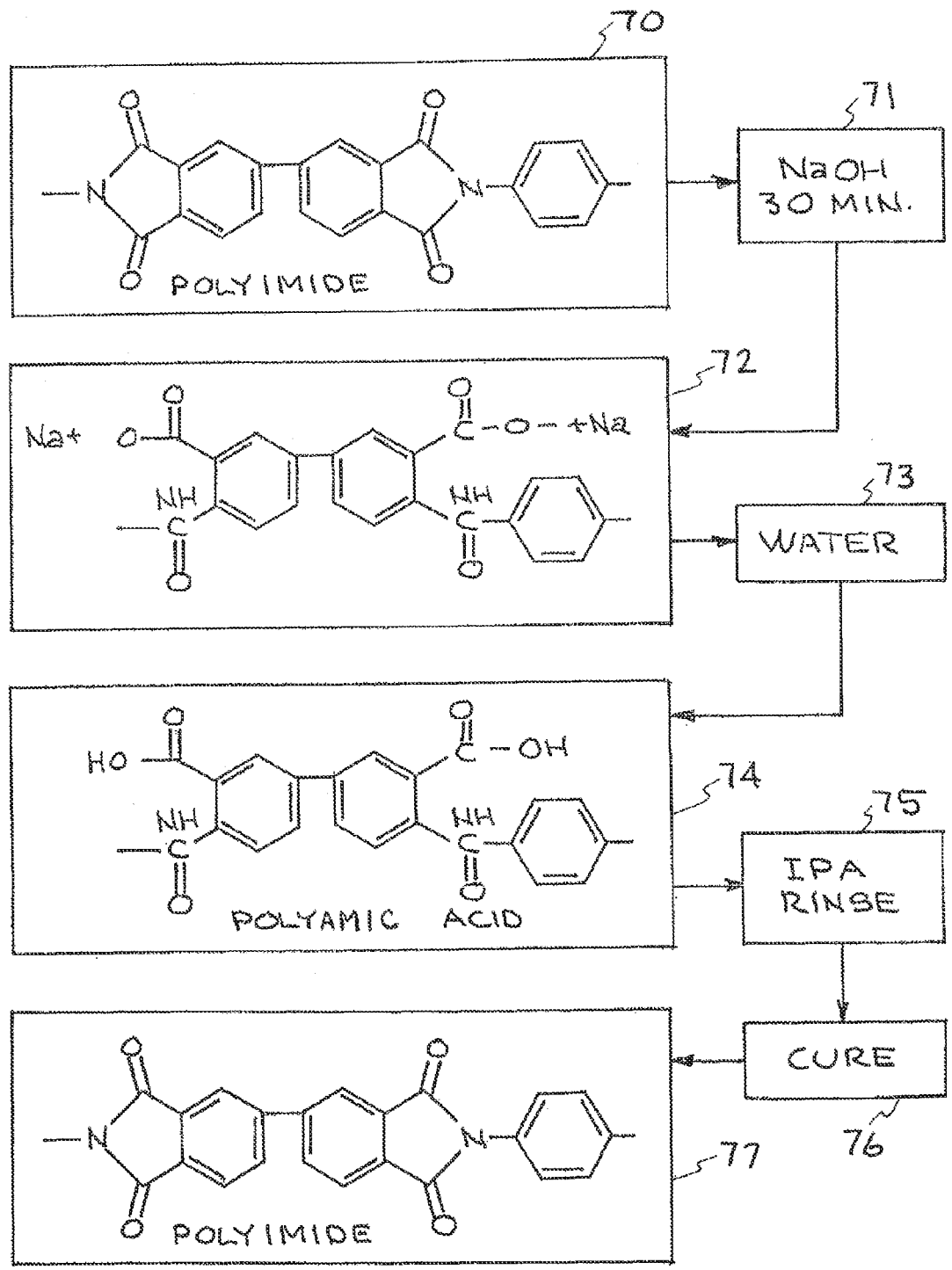
FIG. 23 is a flow diagram of an example embodiment of a process of modifying the surface of a polymer layer prior to depositing a subsequent metal layer to promote adhesion between the layers.

At this point, the surface of the first dielectric layer 11 (including the cavity surfaces) may be modified if desired using either physical or chemical methods to improve and promote the adhesion between the dielectric layer and a subsequently deposited metal or dielectric layer. For polymer-type dielectrics, such as for example polyimide, one example method of modifying the surface involves de-polymerization of the surface followed by deposition of an adhesion promoting layer. In particular, FIG. 23 shows one example method of de-polymerizing the surface of a polyimide layer having a chemical structure shown at reference character 70. As shown at 71, a basic solution such as for example NaOH or KOH is used (e.g. application of NaOH for about 30 minutes shown in FIG. 23) to first de-polymerize the polyimide film and break it down into polyamic acid monomers, as shown at 72. It is appreciated that NaOH may be substituted with KOH, with KOH being more aggressive than NaOH so as to be used in a lower concentration than NaOH. Next the surface is rinsed/treated with water 73 or hydrogen chloride (HCl) (e.g. for about 2-3 minutes) to hydrogenate the surface and remove Na groups, as shown at 74, to thereby passivate the de-polymerized bonds (oxygen groups) so that it is stable for subsequent processing. Isopropyl alcohol (IPA) may then be used to rinse at 75 to remove any excess water and NaOH on the surface. IPA is also used because it will evaporate much quicker than water and at room temperature. After de-polymerization of the surface, an adhesion promoting material may then be deposited on the de-polymerized surface of the polymer layer to bond with the de-polymerized surface (not shown in FIG. 23). The adhesion promoting material may be, for example, any interstitial nitride such as TiN or TaN, SiN, SiC, or any material that forms a covalent bond with the functional groups on polyamic acid, such as for example self-assemble monolayers (SAM) which are typically silane-based and have an amine group on one end and a Silane group on the other to bond to a metal oxide, such as for example $TiO_2$. The polymer film together with the adhesion promoting material layer may then be cured in the curing step shown at 76 to produce the polyimide shown at 77. And for non-polymer dielectric films, de-polymerization is not used. Instead, other adhesion treatments may be used to improve adhesion to a subsequent metal or dielectric layer. In the case of non-polymer dielectric films which either oxidize or are silicon based, SAMs may be used to bond a subsequent polymer layer to the underlying non-polymer dielectric. For example, for coupling/bonding polyimide to a silicon substrate, a SAM preparation known as VM-651 which is an organosilane may be used which has a dichlorosilane group on one end to bond to the silicon substrate and a amino group on the other to bond to the polyimide during a curing process. It is appreciated however that VM-651 will not bond (1) polymerized or de-polymerized polyimide to polymerized or de-polymerized polyimide or (2) polymerized polyimide to silicon. Other adhesion treatments may also be used for adhering other types of un-polymerized polymers to silicon, oxide surface, or other non-polymer dielectrics. For example A-174 silane is an adhesion promoter/coupling agent known for bonding parylene to silicon. It is further appreciated that other physical and chemical methods known in the art may also be employed in the alternative to modify the surface of the dielectric layer to promote adhesion.

Figure 2:
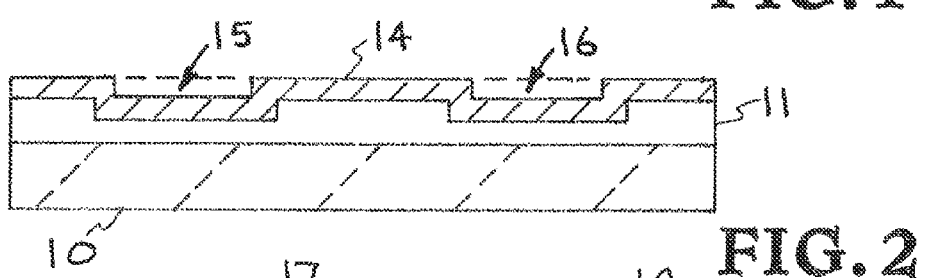

FIG. 2 shows a layer of metal 14 (which may itself be a stack of different metals) deposited on the first dielectric layer 11, using for example but not limited to sputtering and/or evaporation, and/or electroplating techniques. Example metals used may include noble metals such as Pt or Au to metallically bond with the underlying dielectric layer (e.g. that has been previously surface-modified), or other metals such as Ti. If for example a metal is deposited over an adhesion promoting layer (such as Ti over TiN) as described above, then covalent bonds may be formed to promote inter-layer adhesion. It is appreciated that subsequent metal layers may also be deposited using the same or similar techniques. The thickness of the metal layer 14 may be dependent on the particular application intended for the thin film structure/device, and can typically range from a few nanometers to several microns. And the minimum line width of the metal structures produced is only limited to the photolithographic technology used. As can be seen in FIG. 2, portions of the metal layer 14 are recessed into the top-side cavities 12 and 13 to form metal cavities 15 and 16, respectively. It is appreciated, however, that depending on the thickness of the metal layer deposited, the metal cavities may or may not be formed.

Figure 3:
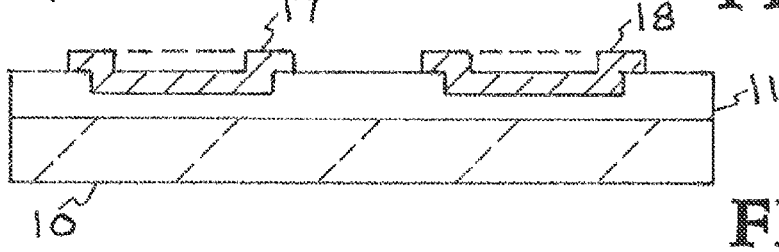

FIG. 3 shows defined metal structures 17 and 18 formed from the first metal layer 14 by etching portions of the metal layer down to the first dielectric layer 11, thereby exposing portions of the first dielectric layer. The metal layer may be etched such as by using photoresist material as a mask (not shown) or in combination with an intermediate masking layer (not shown) of metal or a high temperature polymer. If photoresist is used, it must be of a type capable of withstanding the high temperature and high ion flux (Ar+) from an ion beam in the ion milling process, described next. This ion beam usually carbonizes the photoresist which makes it difficult to remove without using a oxygen plasma which will attack the underlying polymer layer. An alternative to photoresist is the use of a high temperature polymer such as polyimide as an etch mask, and which is capable of surviving temperatures greater than 120 degrees C. It also has to be able to withstand the high energy ion flux from the Argon ions which are bombarding the surface of the mask in the ion milling process. Even if the temperature of the bulk is kept below 120 degrees C., usually the photoresist still carbonizes because the local temperature at the surface still gets high because the energy absorbed due to the ion flux is greater than the heat the photoresist can conduct away to the bulk (the water). A second metal of a different type than the metal layer may also be used as the etch mask. In particular, the selectivity of the mask metal to the underlying metal is important in order to be able to strip the mask metal. For example, Al may be used as a etch mask for Pt and Au because Al etchant does not etch either Au or Pt or Ti or TiN etch. It also does not attack the underlying polymer layers. Lift-off techniques can also be used to deposit defined metal structures on the surface of the first dielectric layer.

In an example embodiment, the thin film structure is placed in an ion mill with a top surface of the structure positioned at an angle of 0 to 90 degrees from the normal incidence of incoming ions. The gas used in the ion mill can be comprised of between 0 to 100% argon. The remaining gas composition can be any combination of gases containing chlorine and/or fluorine atoms and/or compounds. Other gases like helium, hydrogen, and/or oxygen atoms and/or compounds may also be used with the main process gases. The pressure used in the ion mill can process range from 100 torr to $1 \times 10^{-10}$ torr. The power used in the system can range from a few hundred watts to the several kilowatts. The total etch time used in the ion mill can be composed of a single etch cycle or a combination of etch cycles in order to etch underlying metal layer or layers. Other techniques like reactive ion etching, deep reactive ion etching, plasma etching, and/or other dry or wet etching techniques can also be employed. It is appreciated that the formation of additional metal structures in subsequent metal layers may also employ any of the techniques described above as well. Any remnants of the etch mask may be removed at this time using dry and/or wet etch techniques (not shown). Here again, the exposed top surface of the first dielectric layer 11 may then be modified by either physical or chemical methods, such as previously described, in order to improve the adhesion with a subsequent dielectric layer.

Figure 4:
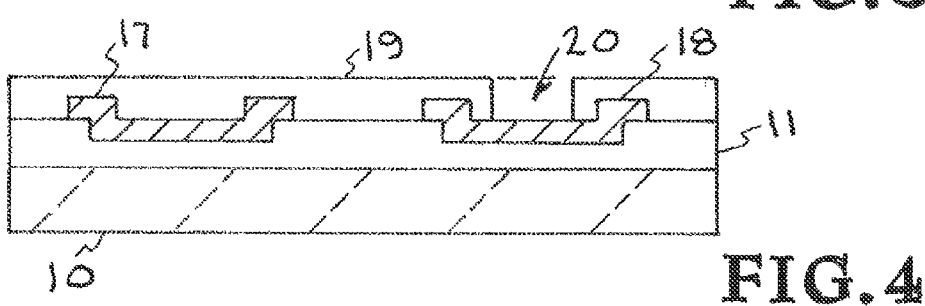

FIG. 4 shows a second dielectric layer 19 deposited over the defined metal structures 17 and 18 and the first dielectric layer 11 using techniques similar to those used to deposit the first dielectric layer 11. The thickness of this deposited second dielectric layer can range from 1 nm to 10 mm, and be made of a material also similar to the first dielectric layer. The device may also be placed under a temperature curing cycle if necessary to cure the second dielectric layer. FIG. 4 also shows an opening 20 formed in the second dielectric layer 19 over the defined metal structure 18 using techniques similar to those used to form cavities 12 and 13. The opening 20 is shown etched completely through the second dielectric layer 19 down to the defined metal structure 18. The opening is a front side opening which exposes a top surface of the defined metal structure 18 to form a front-side electrode or electrical contact or pad. At this point, the overall shape of the device may be defined such as for example using either standard photolithographic techniques in combination with a wet or dry etch technique like but not limited to an $O_2$ plasma or laser ablation (not shown).

Figure 5:
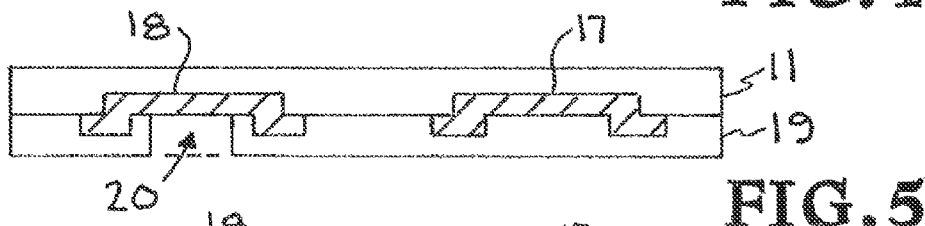

FIG. 5 shows the device structure released from the substrate 10 (no longer shown). The substrate may be released for example by soaking in liquid such as but not limited to water. Elevated temperatures may also be employed to reduce the amount of soaking time necessary before device release. FIG.

5 also shows the device structure flipped (and placed on a separate substrate, not shown), so that a bottom surface of the first dielectric layer 11 (or backside surface of the device/structure) is now positioned/oriented for further processing.

Figure 6:
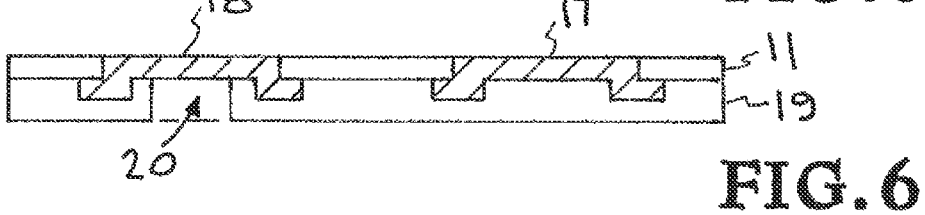

And FIG. 6 shows the device structure after the backside surface of the first dielectric layer 11 is etched down to expose a bottom surface of the defined metal structures 17 and 18, and in particular the cavity-filled portion of the defined metal structures 17 and 18. Generally, a front-side electrode or electrical contact/pad is formed by exposing a top surface of a defined metal structure of an uppermost metal layer, while a back-side electrode or electrical contact/pad is formed by exposing a bottom surface of a defined metal structure of a lowermost metal layer. However, in FIGS. 1-6, the defined metal structures 17 and 18 are part of a single metal layer 19, such that the metal layer 19 is both the uppermost metal layer and the lowermost metal layer, which is an important characterization when contrasted to the fabrication of multi-level thin film structures where an uppermost metal layer is different from a lowermost metal layer.

Figure 7:
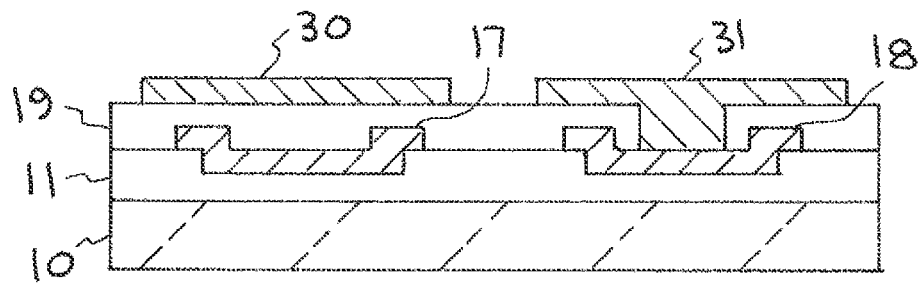
FIGS. 7-9 show three alternative stages to FIGS. 4-6 and following FIGS. 1-3, of an example embodiment of a method for fabricating an example multi-level thin film structure having conductive electrodes on the front and backsides.
Figure 8:
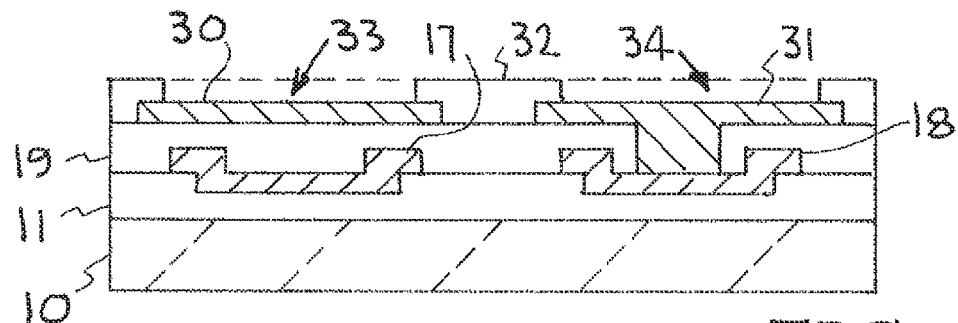
Figure 9:
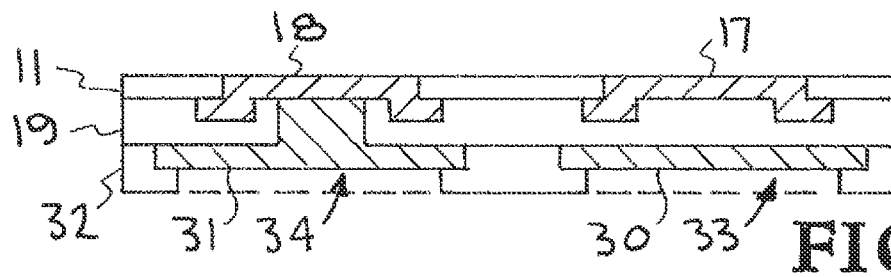

FIGS. 7-9 show three alternative stages to FIGS. 4-6 and following FIGS. 1-3, of an example embodiment of a method for fabricating an example multi-level thin film structure having conductive electrodes on the front and backsides. Generally, after performing the optional modification step of the first dielectric layer described in FIG. 3, additional levels of metal and dielectric layers may be fabricated to form a multi-level thin film device. Generally, for each additional level, another metal layer is deposited on a previous dielectric layer, portions of the another metal layer are etched down to the previous dielectric layer to form another defined metal structure or structures, and another dielectric layer is deposited on the another defined metal structure and exposed portions of the previous dielectric layer. In this way the uppermost metal layer is different from the lowermost metal layer. While FIGS. 7-9 show the formation of one additional level added to the single-level device of FIGS. 1-6, it is appreciated that many more levels may be similarly fabricated in a similar manner.

As particularly shown in FIG. 7, another metal layer is deposited over the second dielectric layer 19 and formed into a second level of defined metal structures 30 and 31 by subsequent ion-milling, for example. Defined metal structure 31 in particular is formed by depositing a portion of the additional metal layer into a via cavity or opening formed on the second dielectric layer 19, to be electrically connected to the defined metal structure 18 in the lower level by the via formed in the via cavity.

And FIG. 8 shows another dielectric layer 32 deposited on the defined metal structures 30 and 31 in addition to the exposed portions of the second dielectric layer 19, using techniques similar to those used to deposit the first dielectric layer 11. The thickness of this deposited dielectric layer can also range from 1 nm to 10 mm, and be made of a material similar to the other first and second dielectric layers. The device may also be placed under a temperature curing cycle if necessary to cure the another dielectric layer. FIG. 8 also shows openings 33 and 34 formed in dielectric layer 32 over the defined metal structures 30 and 31, respectively. This again may be formed by using techniques similar to those used to etch other dielectric layers, and in particular by etching through the dielectric layer 32 down to the defined metal structures 30 and 31. The opening is a front side opening which exposes a top surface of the defined metal structures 30 and 31 to form front-side electrodes or electrical contacts or pads. At this point, the overall shape of the device may be defined as previously described regarding FIG. 4.

And similar to FIGS. 5 and 6, FIG. 9 shows the device structure with the substrate 10 removed, and the device structure flipped and etched on a backside surface (i.e. bottom surface) of the first dielectric surface to expose a bottom surface of the defined metal structures 17 and 18, and in particular the cavity-filled portion of the defined metal structures 17 and 18. Techniques similar to those used to etch the first dielectric layer 11 in FIG. 6 may also be used. In this manner, a front-side electrode or electrical contact/pad is formed by exposing a top surface of a defined metal structure 30 and 31 of an uppermost metal layer, while a back-side electrode or electrical contact/pad is formed by exposing a bottom surface of a defined metal structure 17 and 18 of a lowermost metal layer, to create a multi-level, high density electrode array.

Figure 10:
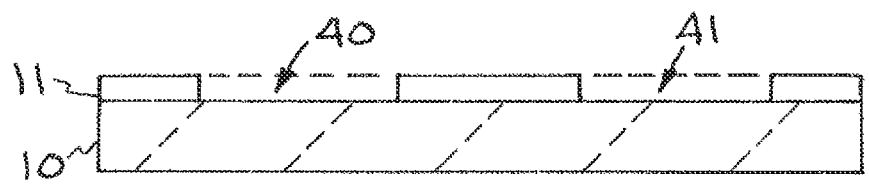
FIGS. 10 and 11 show two alternative stages to FIG. 1, to illustrate the formation of a top-side cavity from a base dielectric layer and a subsequent first dielectric layer, instead of the single dielectric layer of FIG. 1.
Figure 11:
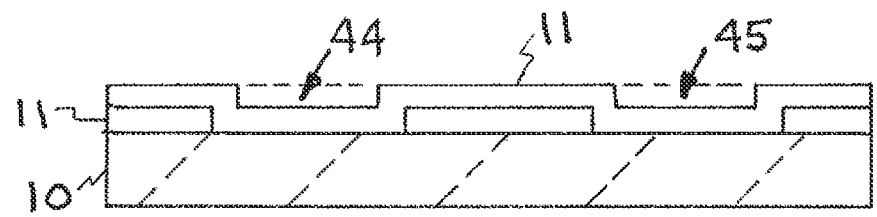

FIGS. 10 and 11 show two alternative stages to FIG. 1 for forming the top-side cavities. In particular, FIGS. 10 and 11 illustrate the formation of two top-side cavities from a base dielectric layer and a subsequent first dielectric layer, instead of the single dielectric layer of FIG. 1. In particular, the top-side cavities 44 and 45 shown in FIG. 11 are formed as follows. First a base dielectric layer 43 is deposited on a substrate 10, following by the formation of a base cavity or cavities 40 and 41 on the base dielectric layer, using photo-lithographic and etching techniques previously described. Preferably, the base dielectric layer 43 is etched down through to the substrate 10 so that the base cavities 40 and 41 are bounded from below by the substrate. The surface of the base dielectric layer 43 may then be modified as previously described to improve the adhesion between it and subsequent dielectric layers. Next, as shown in FIG. 11, the first dielectric layer 11 is deposited on the base dielectric layer 43 so that a portion of the first dielectric layer 11 is recessed into the base cavities 40 and 41 to form the top-side cavities 44 and 45, respectively. At this point, fabrication continues according to the stages described for FIGS. 2-6. It is appreciated, however, that due to the presence of the extra base dielectric layer 43, the step to expose the bottom surface of the cavity-filled portion of the defined metal structure of the lowermost metal layer is performed by releasing the substrate from the base dielectric layer and etching the base dielectric layer and the first dielectric layer to the cavity-filled portion of the metal layer (not shown). It is further appreciated that additional levels may also be added according to the alternative stages shown in FIGS. 7-9 to form multi-level thin film devices.

FIGS. 12-16 show five progressive stages of another example embodiment of a method of fabricating an example single-level thin film structure having conductive electrodes on the front and backsides, and formed in part using a release layer to expose a bottom surface of a defined metal structure. While fabrication of a single-level thin film device and structure is described, it is appreciated that a multi-level device and structure may be produced by fabricating additional levels according to the alternative stages shown in FIGS. 7-9.

Figure 12:
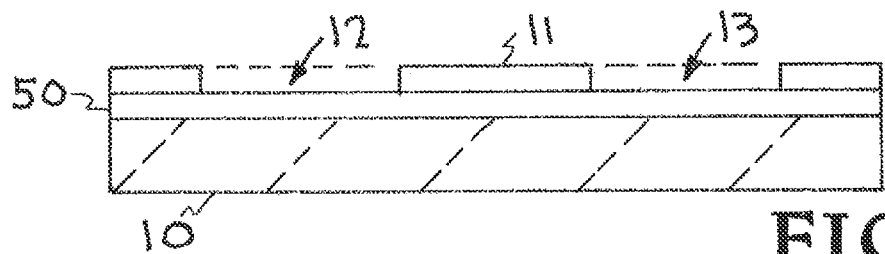
FIGS. 12-16 show five progressive stages of an example embodiment of a method of fabricating an example single-level thin film structure having conductive electrodes on the front and backsides, and formed in part using a release layer to expose a bottom surface of a defined metal structure.

In particular, FIG. 12 shows a release layer 50 first deposited onto a substrate 10 of a type previously described, using for example but not limited to spin, spray, sputtering, evaporation, and/or electroplating techniques. The release layer 50 may be for example but not limited to a metal, a water soluble film, and/or a solvent soluble film. The thickness of the release layer 50 is dependent on the application of the user and can typically range from a few nanometers to several millimeters. FIG. 12 also shows a first dielectric layer 11 deposited on top of the release layer 50 using previously described techniques. The thickness of the first dielectric layer 11 can range from 1 nm to 10 mm, and can then be placed under a temperature curing cycle if necessary. Two top-side cavities 12 and 13 are then formed on a top side surface of the first dielectric layer 11, so that they extend completely through the first dielectric layer 11 down to the underlying release layer 50. At this point, the surface of the first dielectric layer 11 may be modified as previously described to improve the adhesion between the dielectric layer and a subsequent metal layer.

Figure 13:
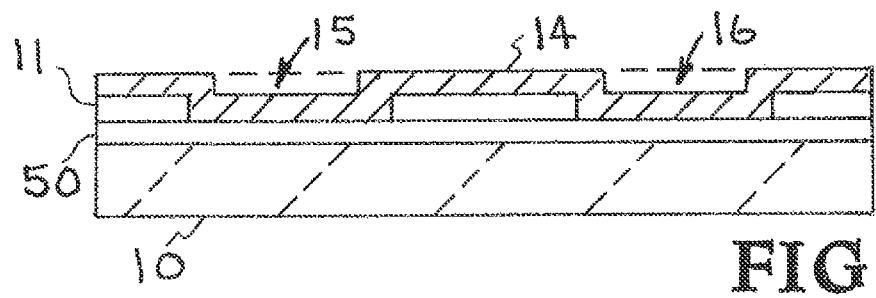

FIG. 13 is similar to FIG. 2, and shows the a layer of metal 14 deposited on the first dielectric layer 11 so that portions of the metal layer 14 are recessed into the top-side cavities 12 and 13 to form metal cavities 15 and 16, respectively.

Figure 14:
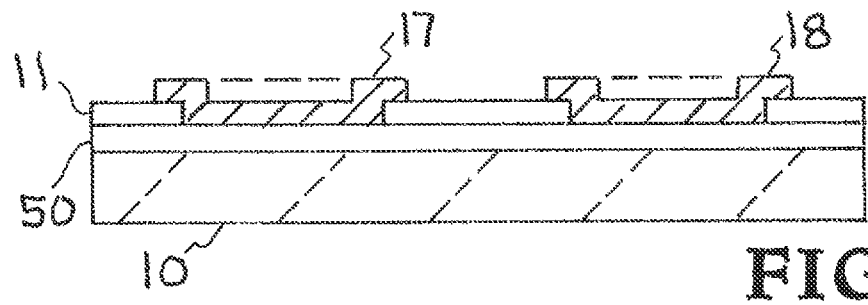

FIG. 14 is similar to FIG. 3, and shows defined metal structures 17 and 18 formed from the first metal layer 14 by etching (e.g. ion milling) portions of the metal layer down to the first dielectric layer 11, thereby exposing portions of the first dielectric layer. Any remnants of the etch mask may be removed at this time using dry and/or wet etch techniques (not shown). Here again, the exposed top surface of the first dielectric layer 11 may then be modified by either physical or chemical means/methods in order to improve the adhesion with a subsequent dielectric layer.

Figure 15:
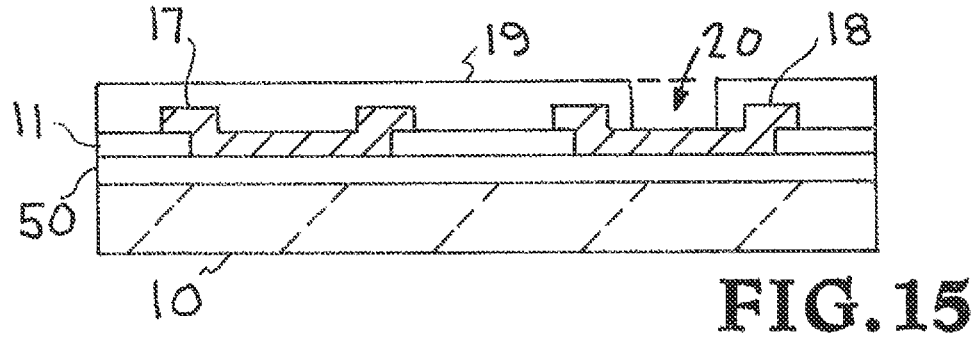

FIG. 15 is similar to FIG. 4, and shows a second dielectric layer 19 deposited over the defined metal structures 17 and 18 and the first dielectric layer 11, and an opening 20 formed in and completely through the second dielectric layer 19 down to the defined metal structure 18 to expose a top surface of the defined metal structure 18 and form a front-side electrode or electrical contact or pad. At this point, the overall shape of the device may be defined as previously described.

Figure 16:
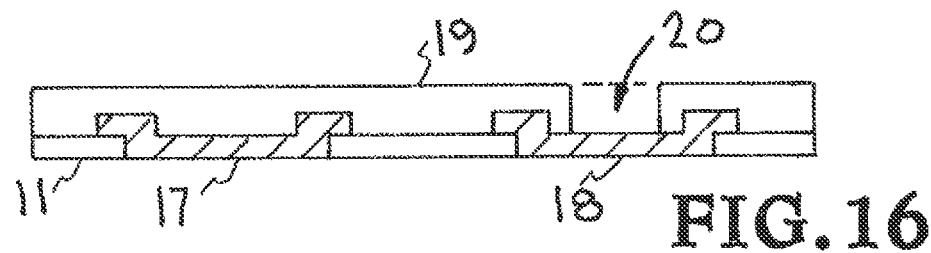

FIG. 16 shows the device structure released from the substrate 10 (no longer shown) by soaking in a release etchant. Because the release layer 50 bounded the cavity-filled portion of the defined metal structures 17 and 18 in FIG. 15, removing the release layer to lease the substrate functions to expose the bottom surface of the metal layer 14 (i.e. the lowermost metal layer).

And FIGS. 17-22 show six progressive stages of an example embodiment of a method of fabricating an example single-level thin film structure having conductive electrodes on the front and backsides, and formed in part using bumps under a release layer to expose a bottom surface of a defined metal structure. Here too, while fabrication of a single-level thin film device and structure is described, it is appreciated that a multi-level device and structure may be produced by fabricating additional levels according to the alternative stages shown in FIGS. 7-9.

Figure 17:
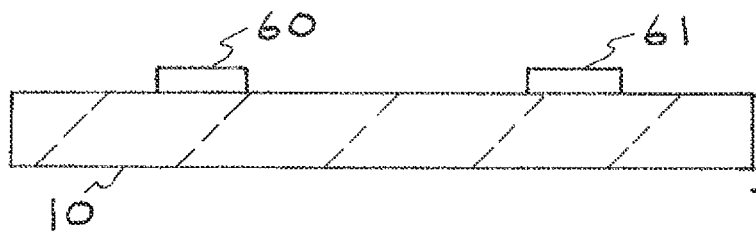
FIGS. 17-22 show six progressive stages of an example embodiment of a method of fabricating an example single-level thin film structure having conductive electrodes on the front and backsides, and formed in part using bumps formed under a release layer to expose a bottom surface of a defined metal structure.

In particular, FIG. 17 shows two bumps 60 and 61 formed on a substrate 10. The bumps may be formed for example by depositing and subsequently etching a hump layer of a material type such as but not limited to nitride, oxide, poly-silicon, polymers, and or metal. The thickness of the bump layer deposited can range from 1 nm to 10 mm. In the alternative, the bumps may be formed by etching the substrate while keeping the electrode areas protected by the etch mask (not shown).

Figure 18:
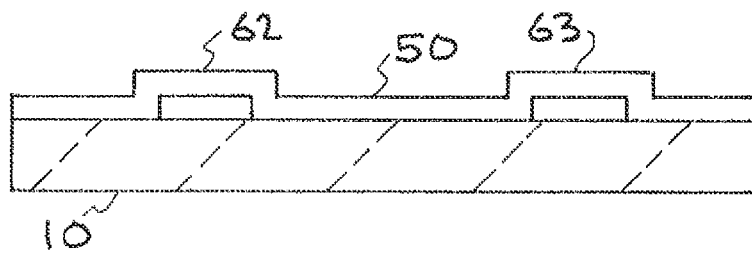

FIG. 18 shows a release layer 50 deposited over the bumps 60 and 61 and the substrate 10 to produce raised bumped portions 62 and 63, respectively, which rise above/protrude higher than non-bumped portions of the release layer. Similar to the embodiment of FIGS. 12-16, the release layer 50 may be for example but not limited to a metal, a water soluble film, and/or a solvent soluble film. The thickness of the release layer 50 is dependent on the application of the user and can typically range from a few nanometers to several millimeters.

Figure 19:
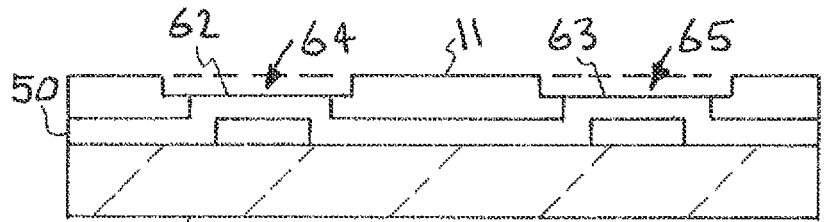

FIG. 19 shows a first dielectric layer 11 deposited on top of the release layer 50 using previously described techniques, with two top-side cavities 64 and 65 formed on a top side surface of the first dielectric layer 11 so that they extend completely through the first dielectric layer 11 down to the bumped portions 62 and 63 of the underlying release layer. At this point, the surface of the first dielectric layer 11 may be modified as previously described to improve the adhesion between the dielectric layer and a subsequent metal layer.

Figure 20:
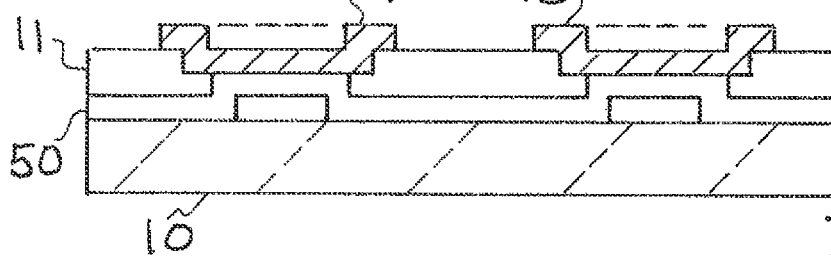

FIG. 20 is similar to FIGS. 3 and 14, and shows defined metal structures 17 and 18 formed from a first metal layer by etching (e.g. ion milling) portions of the metal layer down to the first dielectric layer 11, thereby exposing portions of the first dielectric layer. The defined metal structures 17 and 18 include portions of the metal layer which fill the top-side cavities 64 and 65, respectively, and are bounded on the bottom by the bumped portions 62 and 63, respectively, of the release layer. Any remnants of the etch mask may be removed at this time using dry and/or wet etch techniques (not shown). Here again, the exposed top surface of the first dielectric layer 11 may then be modified by either physical or chemical means/methods in order to improve the adhesion with a subsequent dielectric layer.

Figure 21:
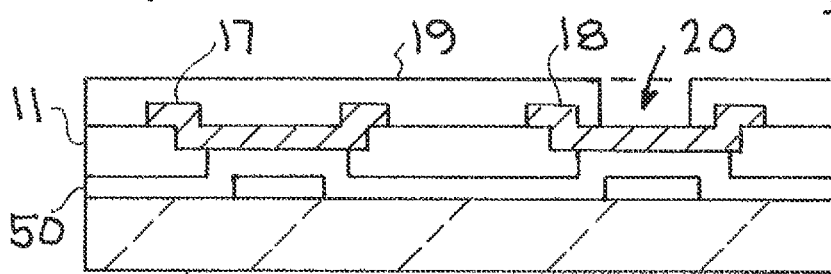

FIG. 21 is similar to FIGS. 4 and 15, and shows a second dielectric layer 19 deposited over the defined metal structures 17 and 18 and the first dielectric layer 11, and an opening 20 formed in and completely through the second dielectric layer 19 down to the defined metal structure 18. This exposes a top surface of the defined metal structure 18 to form a front-side electrode or electrical contact or pad. At this point, the overall shape of the device may be defined as previously described.

Figure 22:
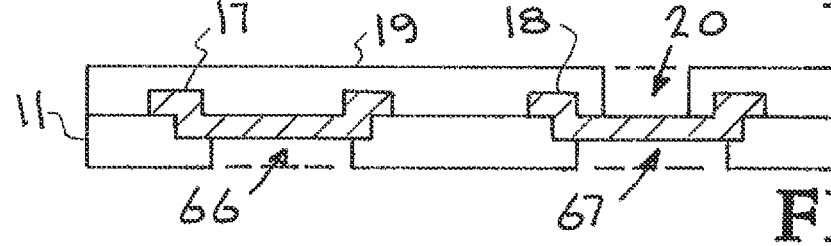

And FIG. 22 is similar to FIG. 16 and shows the device structure released from the substrate 10 (no longer shown) by soaking in a release etchant. Because the release layer 50 bounded the cavity-filled portion of the defined metal structures 17 and 18 in FIG. 15, removing the release layer to lease the substrate functions to expose the bottom surface of the metal layer (i.e. the lowermost metal layer). The difference between the final thin film device shown in FIG. 22 and the final thin film device shown in FIG. 16 is that the exposed bottom surfaces of the defined metal structures 17 and 18 are recessed from a bottom surface of the first dielectric layer 11, as a result of the bumped portions of the release layer.

While particular operational sequences, materials, temperatures, parameters, and particular embodiments have been described and or illustrated, such are not intended to be limiting. Modifications and changes may become apparent to those skilled in the art, and it is intended that the invention be limited only by the scope of the appended claims.

We claim:

1. A method of fabricating a thin film structure having conductive electrodes on both front and back sides thereof, comprising:
    forming a top-side cavity on a first polymer layer;
    depositing a metal layer on the first polymer layer so that a portion of the metal layer fills the cavity;
    etching portions of the metal layer down to the first polymer layer to form a defined metal structure which includes the cavity-filled portion of the metal layer;
    depositing a second polymer layer on the defined metal structure and exposed portions of the first polymer layer;
    exposing a top surface of a defined metal structure of an uppermost metal layer to form a front-side electrode; and
    exposing a bottom surface of a cavity-filled portion of a defined metal structure of a lowermost metal layer to form a back-side electrode.

2. The method of claim 1, further comprising:
    prior to exposing the top and bottom surfaces to form the front-side and back-side electrodes, respectively, forming at least one additional level of metal and polymer layers on the second polymer layer by, for each additional level:
depositing another metal layer on a previous polymer layer;
etching portions of the another metal layer down to the previous polymer layer to form another defined metal structure;
depositing another polymer layer on the another defined metal structure and exposed portions of the previous polymer layer,
whereby the uppermost metal layer is different from the lowermost metal layer.

3. A method of fabricating a thin film structure having conductive electrodes on both front and back sides thereof, comprising:
forming a top-side cavity on a first dielectric layer;
depositing a metal layer on the first dielectric layer so that a portion of the metal layer fills the cavity;
etching portions of the metal layer down to the first dielectric layer to form a defined metal structure which includes the cavity-filled portion of the metal layer;
depositing a second dielectric layer on the defined metal structure and exposed portions of the first dielectric layer;
forming at least one additional level of metal and dielectric layers on the second dielectric layer by, for each additional level: depositing another metal layer on a previous dielectric layer of a previous level; etching portions of the another metal layer down to the previous dielectric layer to form another defined metal structure; and depositing another dielectric layer on the another defined metal structure and exposed portions of the previous dielectric layer, whereby an uppermost metal layer is different from a lowermost metal layer, and for at least one additional level, prior to depositing the another metal layer on the previous dielectric layer, forming a via cavity extending completely through the previous dielectric layer down to a defined metal structure, so that a via is formed when the another metal layer is deposited on the previous dielectric layer with a portion of the another metal layer filling the via cavity;
exposing a top surface of a defined metal structure of the uppermost metal layer to form a front-side electrode; and
exposing a bottom surface of a cavity-filled portion of a defined metal structure of the lowermost metal layer to form a back-side electrode.

4. The method of claim 1,
wherein ion milling is used to etch the portions of the metal layer down to the first polymer layer to form the defined metal structure.

5. The method of claim 1,
wherein the top-side cavity is formed to extend only partially through the first polymer layer.

6. The method of claim 5,
wherein the first polymer layer is deposited on a substrate, and the bottom surface of the cavity-filled portion of the defined metal structure of the lowermost metal layer is exposed by releasing the substrate from the first polymer layer and etching the first polymer layer to the cavity-filled portion of the metal layer.

7. The method of claim 1,
wherein the top-side cavity is formed on the first polymer layer by: depositing a base dielectric layer on a substrate, forming a base cavity on the base dielectric layer, and depositing the first polymer layer on the base dielectric layer so that a portion of the first polymer layer is recessed into the base cavity to form the top-side cavity.

8. The method of claim 7,
wherein the base cavity is formed to extend completely through the base dielectric layer down to the substrate.

9. The method of claim 7,
wherein the bottom surface of the cavity-filled portion of the defined metal structure of the lowermost metal layer is exposed by releasing the substrate from the base dielectric layer and etching the base dielectric layer and the first polymer layer to the cavity-filled portion of the metal layer.

10. A method of fabricating a thin film structure having conductive electrodes on both front and back sides thereof, comprising:
depositing a release layer on a substrate and depositing a first dielectric layer on the release layer;
forming a top-side cavity on the first dielectric layer so as to extend completely through the first dielectric layer down to the release layer;
depositing a metal layer on the first dielectric layer so that a portion of the metal layer fills the cavity;
etching portions of the metal layer down to the first dielectric layer to form a defined metal structure which includes the cavity-filled portion of the metal layer;
depositing a second dielectric layer on the defined metal structure and exposed portions of the first dielectric layer;
exposing a top surface of a defined metal structure of an uppermost metal layer to form a front-side electrode; and
exposing bottom surface of a cavity-filled portion of a defined metal structure of a lowermost metal layer by removing the release layer to release the substrate so as to form a back-side electrode.

11. The method of claim 10,
further comprising forming a bump on the substrate prior to depositing the release layer so that a bumped portion of the release layer covering the bump protrudes higher than non-bumped portions of the release layer.

12. A method of fabricating a thin film structure having conductive electrodes on both front and back sides thereof, comprising:
depositing a release layer on a substrate;
depositing a first dielectric layer on the release layer;
forming a top-side cavity on the first dielectric layer so as to extend completely through the first dielectric layer down to the release layer;
depositing a metal layer on the first dielectric layer so that a portion of the metal layer fills the cavity;
etching portions of the metal layer down to the first dielectric layer to form a defined metal structure which includes the cavity-filled portion of the metal layer;
depositing a second dielectric layer on the defined metal structure and exposed portions of the first dielectric layer;
forming at least one additional level of metal and dielectric layers on the second dielectric layer by, for each additional level: forming a via cavity extending completely through the dielectric layer down to the defined metal structure, so that a via is formed when the another metal layer is deposited on the previous dielectric layer with a portion of the another metal layer filling the via cavity; depositing another metal layer on a previous dielectric layer; etching portions of the another metal layer down to the previous dielectric layer to form another defined metal structure; depositing another dielectric layer on the another defined metal structure and exposed portions of the previous dielectric layer, whereby the uppermost metal layer is different from the lowermost metal layer;

exposing a top surface of a defined metal structure of an uppermost metal layer to form a front-side electrode; and removing the release layer to release the substrate and expose the bottom surface of the cavity-filled portion of the defined metal structure of the lowermost metal layer as a back-side electrode.

13. The method of claim 12, further comprising forming a bump on the substrate prior to depositing the release layer so that a bumped portion of the release layer covering the bump protrudes higher than non-bumped portions of the release layer.

* * * * *